Figure 1:
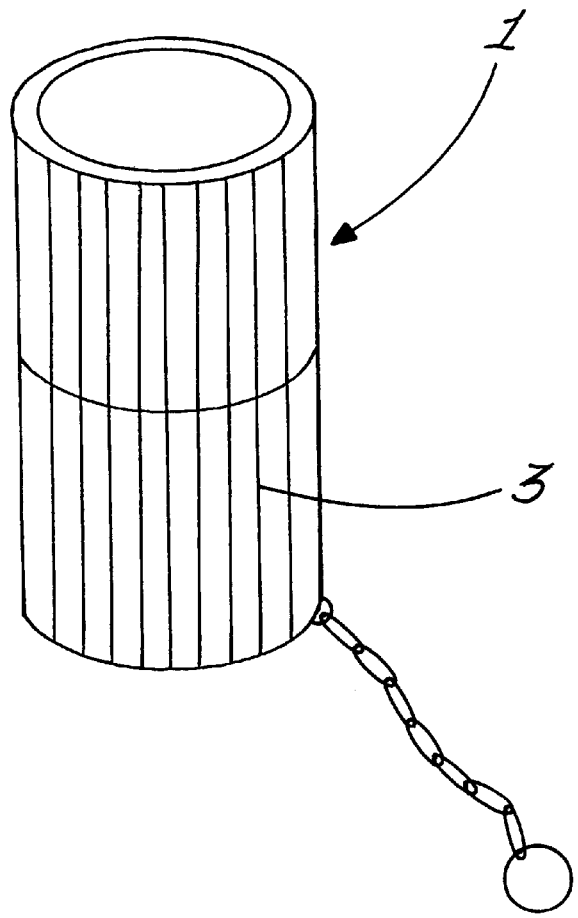

United States Patent
Feuchtgruber

[19]

[11] Patent Number: 6,109,263

[45] Date of Patent: Aug. 29, 2000

[54] PACKAGED RESPIRATORY MASK

[76] Inventor: Gottfried Feuchtgruber, Lindwurmstrasse 12, 80337 München, Germany

[21] Appl. No.: 09/460,355

[22] Filed: Dec. 13, 1999

Related U.S. Application Data

[63] Continuation of application No. 09/018,242, Feb. 3, 1998, abandoned, and a continuation of application No. PCT/DE96/01509, Aug. 6, 1996.

[30] Foreign Application Priority Data

Aug. 9, 1995 [DE] Germany ............................ 195 29 322

[51] Int. Cl.⁷ ..................................................... A62B 18/02
[52] U.S. Cl. ................................. 128/206.28; 128/206.12; 128/206.21; 206/803; 206/815
[58] Field of Search ........................ 128/202.28, 202.79, 128/203.11, 206.12, 206.15, 206.19, 206.21, 206.24, 206.28, 206.29, 207.12; 70/457; 206/803, 815, 824; 222/541.6

[56] References Cited

U.S. PATENT DOCUMENTS

| | | | |
|---|---|---|---|
| 3,358,913 | 12/1967 | Beesley | 230/134 |
| 4,269,315 | 5/1981 | Boyce . | |
| 4,726,365 | 2/1988 | Jablonski . | |
| 4,803,981 | 2/1989 | Vickery | 128/206.24 |
| 4,819,627 | 4/1989 | Connors . | |
| 4,834,085 | 5/1989 | Webster, II | 128/203.11 |
| 5,020,529 | 6/1991 | Gobin | 128/202.28 |
| 5,121,745 | 6/1992 | Israel | 128/202.28 |
| 5,127,397 | 7/1992 | Kohnke | 128/202.28 |
| 5,161,523 | 11/1992 | Gilbert | 128/202.28 |
| 5,295,478 | 3/1994 | Bladwin | 128/203.11 |
| 5,388,570 | 2/1995 | Wassil | 128/200.24 |
| 5,535,736 | 7/1996 | Jzaw | 128/202.26 |
| 5,735,265 | 4/1998 | Flynn | 128/203.11 |
| 5,765,551 | 6/1998 | Sugino | 128/203.11 |
| 5,813,423 | 9/1998 | Kirchgeorg | 128/202.28 |

FOREIGN PATENT DOCUMENTS

| | | |
|---|---|---|
| 350 914 | 1/1990 | European Pat. Off. . |
| 19 44 548 | 3/1971 | Germany . |
| 2 244 887 | 2/1972 | Germany . |
| 23 18 914 | 10/1974 | Germany . |
| 26 52 128 | 12/1977 | Germany . |
| 35 43 931 | 6/1987 | Germany . |
| 87 09 867 | 10/1987 | Germany . |
| 42 12 259 | 1/1993 | Germany . |
| 43 12 215 | 4/1994 | Germany . |
| 42 41 272 | 8/1994 | Germany . |
| 43 11 309 | 9/1994 | Germany . |
| 43 44 403 | 10/1994 | Germany . |
| 433023 | 9/1967 | Switzerland . |
| 841104 | 7/1960 | United Kingdom . |
| 93/16747 | 9/1993 | WIPO . |

OTHER PUBLICATIONS

Ambu Mark III Beatmungsbeutel Brochure, 5 pgs, Jul. 15, 1995, Abstract.
Dyna Med Catalog 1030, Spring 1994, 3 pgs.
International Search Report.

*Primary Examiner*—John G. Weiss
*Assistant Examiner*—Joseph F. Weiss, Jr.
*Attorney, Agent, or Firm*—Fitch, Even, Tabin & Flannery

[57] ABSTRACT

An apparatus is described for the emergency respiration of a patient which is packed to be very small and which achieves the state of use of the respiratory mask in routine operation through volume growth of a foam body.

6 Claims, 1 Drawing Sheet

U.S. Patent Aug. 29, 2000 6,109,263

PACKAGED RESPIRATORY MASK

This is a continuation of prior application Ser. No. 09/018,242, filed Feb. 3, 1998 now abandoned, which is hereby incorporated herein by reference in its entirety. This application is a continuation of Ser. No. PCT/DE96/01509 filed Aug. 6, 1996.

The invention relates to a packaged respiratory mask in accordance with the preamble of patent claim 1, which enables the user to give artificial respiration from mouth to mouth, mouth to nose or with a respiratory bag without contact to skin, mucous membranes or body secretions. A respiratory mask of this kind is known from U.S. Pat. No. 5,121,745. This known mask is self-inflating and has a bladder which can be filled with air.

Respiratory masks are basically known in the most diverse fields of medicine, in particular in the fields of anaesthetics and emergency medicine. These masks normally cover over the mouth and nose region and consist of elastic material. The masks are lightly pressed in place by hand or held by straps. Such masks are known from GB-PS 841 104, DE 42 12 259 C1, DE 43 12 215 C1 or from U.S. Pat. No. 3,358,913.

In situations of attempted resuscitation the first helper is required to give mouth to mouth or mouth to nose respiration to maintain the supply of oxygen, assuming that no appropriate medical apparatus is available on site. This can give rise to the transmission of infectious diseases through the body contact. Prior to the insertion of a resuscitation tube into the trachea the respiration is carried out by specialist personnel by means of a mask which surrounds the mouth and nose, is of bell shape and is outwardly sealed by a bead and by a compressible balloon connected thereto with an oxygen line.

Various aids have been offered to the first helper as protection against contamination. These aids are either characterised by a bulky packaging volume or by an inadequate protection against contamination (covering of the mouth and nose by a foil). Some have a mouthpiece which must be inserted deep into the patient's mouth (DE-GM 87 09 867).

A respiratory mask of integral foam is known from DE-OS 22 44 887, having a plexi-glass stiffener extending in its interior.

The problem (object) underlying the invention is to further develop a respiratory mask of the initially named kind in such a way that it is simple to manufacture and adopts a smaller packaged volume in the compressed state.

This object is satisfied by the features of patent claim 1.

Through the solution of the invention a mask is provided which in the unused state can be packed to be very small (key-ring principle) and which is simultaneously light and easy to handle. The mask does not involve any danger of injury for the patient and is equivalent in the state ready for use to a normal respiratory mask. It can thus continue to be used by the specialist personnel after resuscitation has been started by the first helper until the insertion of a respiratory hose. On the other hand, the mask of the invention can replace the hitherto known and relatively bulky masks in emergency equipment which must be packed to be very small (mountain rescue, helicopter, expeditions, . . . ).

Advantageous embodiments of the invention are described in the subordinate claims.

The housing can correspond in its dimensions approximately to a film cartridge. The foam body can be compressed by means of vacuum and welded into a foil. By interrupting the vacuum the mask can be brought quickly in seconds into the form ready for use. It is also conceivable to allow the mask shape to arise and to cure by the foaming of two liquid foam components in the pre-shaped foil.

It is thus important for the apparatus of the invention that instead of the previously used bulky masks or small masks without adequate protection, one now works with a compressible foam body which, in the state ready for use, strongly resembles the respiratory mask used everyday in clinics for the introduction of an anaesthetic. In this way the acceptance by the specialist personnel is increased. Through the small packaging volume users are encouraged to continuously take it with them (key-ring principle), which is advantageous in as much as situations where resuscitation is necessary can always occur anywhere. The accommodation of a respiratory mask in the first aid box of a motorcar is generally inadequate.

The housing should have seams where it is intended to rupture. Furthermore, a filter or a non-return valve can be provided in the dome region of the mask whereby additional protection against contamination also arises with mouth to mask respiration.

The mask of the invention is a disposable article. As a recycling measure the foam body can, however, be introduced anew into a new foil after separation from a foil enclosing it and after appropriate cleaning.

Figure 2:
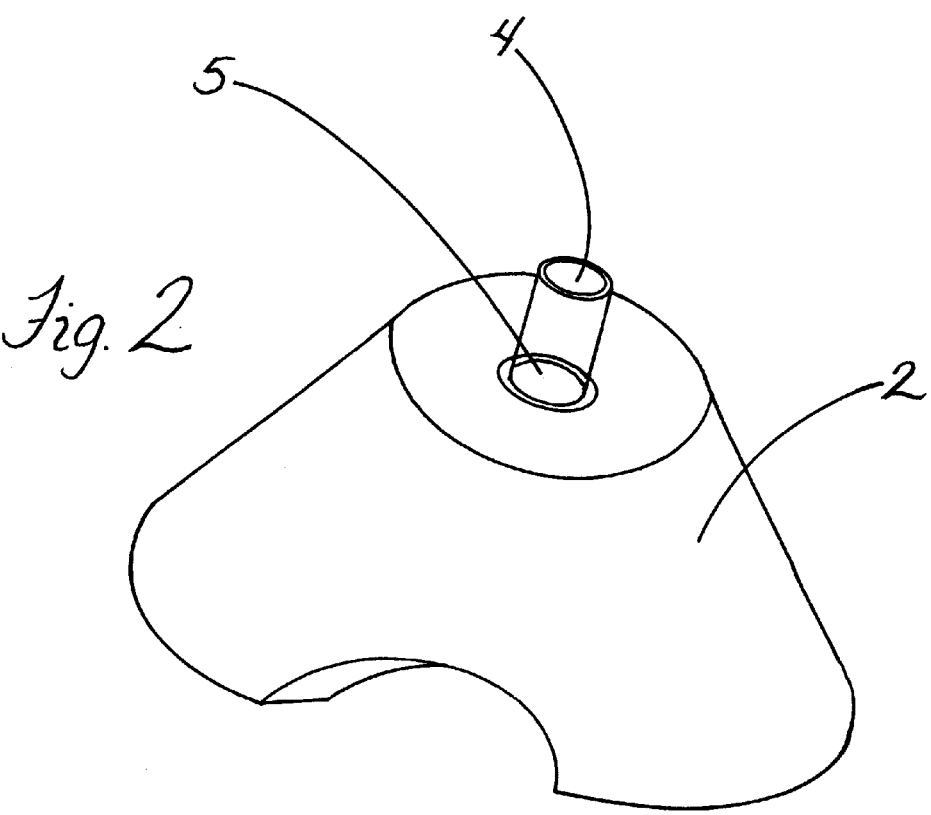

An embodiment of the invention will be explained purely by way of example with reference to the accompanying drawings. There are shown:

FIG. 1 a perspective view of a packaged respiratory mask in accordance with the invention; and FIG. 2 a perspective view of a respiratory mask in accordance with the invention in its state of use.

FIG. 1 shows a housing 1 in which the compressed respiratory mask is located, which has, for example, in practice a base area of 4 cm in diameter and a height of about 5 cm. The compressed foam body 2 (see FIG. 2) is welded into foil in this housing which consists of foil material. The housing 1 can be opened by opening the seams 3 of intended rupture.

As can be seen from FIG. 1 the seams of intended rupture 3 which are worked into the foil extend parallel to one another and to the cylindrical jacket surface of the housing 1. A further seam of intended rupture is provided in the centre of the housing 1 and is formed as a circumferential seam. In this way the housing can be very easily opened in as much as the two housing halves which lie on both sides of the circumferential seam can be grasped with one hand in each case and twisted relative to one another. In this way the seams of desired breakage 3 of the housing 1 abruptly rupture so that the foam body of the respiratory mask can expand. As long as the respiratory mask is located in its compressed state in the housing it is easy to transport. For this purpose a key ring or key pendant (FIG. 1) can be provided which is secured to the housing.

FIG. 2 shows the respiratory mask 2 of the invention in its state of use. A normed opening 4 is provided at the top side of the mask through which respiratory gas can be blown in. A non-return valve 5 is located beneath this opening 4.

The shape of the welded-in foam body (FIG. 1) corresponds in its state of use (FIG. 2) to an approximately triangular, peripherally extending bead (dome-like bell) for sealing against the face which is arched over by a dome-like bell. Thus the mask can be sealingly pressed against the face surrounding the mouth and nose without the mouth or nose being restricted. Air can be blown into the mask and thus into the mouth or the nose of the patient via an attached bag or via a resuscitation hose or with the aid of the mouth.

What is claimed is:

1. A packagable respiratory mask system comprising:
   a respiratory mask having a shape-retentive body of a compressible foam material, the body having a first inoperative state in which the body is compressed for transport and a second operative state where the body expands to a predetermined size and shape for use about the mouth and nose of a human;
   a housing which contains the mask foam body in the first state, the housing having predetermined dimensions that restrain the shape-retentive mask foam body from expanding from the first state to the second state at a size slightly smaller than the housing's predetermined dimensions; and
   a release mechanism on the housing operable to allow release of the mask foam body from the restraint of the housing so that the shape-retentive body shifts from the first inoperable state to the second operable state.

2. A packagable respiratory mask system as defined in claim 1, wherein the release mechanism comprises rupturable seams on the housing.

3. A packagable respiratory mask system as defined in claim 1, wherein the housing has the dimensions of about 4 cm in diameter and about 5 cm in height.

4. A packagable respiratory mask system as defined in claim 1, wherein the housing comprises foil.

5. A packagable respiratory mask system as defined in claim 4, wherein the foil has rupturable seams.

6. A packagable system as defined in claim 1, wherein the body is of the compressible foam material for its entire extent so that all portions of the body can be compressed to reduce the body from the predetermined size of the second operative state to the first inoperative state.

* * * * *